(12) United States Patent
Kobayashi et al.

(10) Patent No.: US 10,591,483 B2
(45) Date of Patent: Mar. 17, 2020

(54) DATA ACQUISITION METHOD FOR DETERMINING LIKELIHOOD THAT OVARIAN ENDOMETRIOTIC CYST IS CANCEROUS, AND DIAGNOSTIC DEVICE FOR SAME

(71) Applicant: CELLSPECT CO., LTD., Morioka, Iwate (JP)

(72) Inventors: Hiroshi Kobayashi, Kashiwara (JP); Chiharu Yoshimoto, Kashiwara (JP); Junko Takahama, Kashiwara (JP); Takuya Iwabuchi, Chiba (JP)

(73) Assignee: CELLSPECT CO., LTD., Morioka, Iwate (JP)

( * ) Notice: Subject to any disclaimer, the term of this patent is extended or adjusted under 35 U.S.C. 154(b) by 0 days.

(21) Appl. No.: 15/129,759

(22) PCT Filed: Mar. 27, 2015

(86) PCT No.: PCT/JP2015/059693
§ 371 (c)(1),
(2) Date: Sep. 27, 2016

(87) PCT Pub. No.: WO2015/147284
PCT Pub. Date: Oct. 1, 2015

(65) Prior Publication Data
US 2017/0131284 A1    May 11, 2017

(30) Foreign Application Priority Data
Mar. 28, 2014   (JP) .................. 2014-070166

(51) Int. Cl.
| G01N 33/574 | (2006.01) |
| A61B 8/08 | (2006.01) |
| A61B 5/00 | (2006.01) |
| G01N 33/84 | (2006.01) |
| A61B 8/12 | (2006.01) |

(52) U.S. Cl.
CPC ..... *G01N 33/57442* (2013.01); *A61B 5/4325* (2013.01); *A61B 8/085* (2013.01); *A61B 8/12* (2013.01); *G01N 33/84* (2013.01)

(58) Field of Classification Search
CPC .......... G01N 33/57442; G01N 33/721; G01N 33/726; G01N 33/84; A61B 5/4325;
(Continued)

(56) References Cited

U.S. PATENT DOCUMENTS

2006/0247536 A1* 11/2006 Koski .................. A61B 5/0075
                                                                  600/478
2007/0160973 A1*  7/2007 Burns .................... G01N 21/31
                                                                      435/4
(Continued)

FOREIGN PATENT DOCUMENTS

| JP | 4-138147 A | 5/1992 |
| JP | 2004-337320 A | 12/2004 |
| JP | 2008-506123 A | 2/2008 |

OTHER PUBLICATIONS

Kim, Nam-Ho et al. "Increased ferric iron content and iron-induced oxidative stress in the brains of scapie-infected mice." Brain Research (2000) 884 98-103. (Year: 2000).*

(Continued)

*Primary Examiner* — Christopher Adam Hixson
(74) *Attorney, Agent, or Firm* — Sughrue Mion, PLLC (57) ABSTRACT

[Problem]
To provide a method for acquisition of data able to serve as an index for determining the likelihood that an ovarian endometriosis cyst is cancerous.

Solution
This data acquisition method for determining the likelihood that an ovarian endometriosis cyst is cancerous includes an iron concentration measurement step for measuring the iron concentration in the cystic fluid of the ovarian endometriosis (Continued)

cyst. This diagnostic device for diagnosing the likelihood that an ovarian endometriosis cyst is cancerous is provided, at a minimum, with an iron concentration measurement unit for measuring the iron concentration in the cystic fluid of the ovarian endometriosis cyst.

12 Claims, 3 Drawing Sheets

(58) Field of Classification Search
CPC .............. A61B 5/0075; A61B 5/14507; A61B 5/14546; A61B 8/085; A61B 8/12
See application file for complete search history.

(56) References Cited

U.S. PATENT DOCUMENTS

| | | | |
|---|---|---|---|
| 2008/0161674 A1* | 7/2008 | Monro | G01N 21/31 600/410 |
| 2009/0043174 A1 | 2/2009 | Jarrell | |
| 2011/0082375 A1* | 4/2011 | Sakhel | A61B 1/303 600/462 |

OTHER PUBLICATIONS

Yamaguchi, Ken et al. "Contents of endometriotic cysts, especially the high concentration of free iron, are possible cause of carcinogenesis in the cysts through the iron-induced persistent oxidative stress." Clin. Cancer Res. (2008) 14 32-40. (Year: 2008).*
Cardenas-Turanzas, Marylou et al. "The clinical effectiveness of optical spectroscopy for the in vivo diagnosis of cervical intraepithelial neoplasia: Where are we?" Gynecologic Oncology (2007) S138-S146. (Year: 2007).*
International Search Report dated Jun. 30, 2015 in counterpart international application No. PCT/JP2015/059693.
Written Opinion dated Jun. 30, 2015 in counterpart international application No. PCT/JP2015/059693.
Iizuka et al., "Chemical Assay of Iron in Ovarian Cysts: A New Diagnostic Method to Evaluate Endometriotic Cysts", Gynecologic and Obstetric Investigation, vol. 46, 1998, pp. 58-60.
Yamaguchi et al., "Oxidative stress caused by contents of endometriotic cysts containing iron can be a possible cause of carcinogeriesis in the cysts", The Journal of the Japan Society for Cancer Therapy, vol. 41, No. 2, 2006, p. 539, OS80-1. (2 pages total).
Della Rovere et al., "Hemoglobin Oxidative Stress in Cancer", Anticancer Research, vol. 15, 1995, pp. 2089-2095.
Bandai et al., Japan Society of Endometriosis Journal, vol. 31, 2010, pp. 65-69.
Kobayashi et al., "The role of iron in the pathogenesis of endometriosis", Gynecological Endocrinology, Jan. 2009, vol. 25, No. 1, pp. 39-52. (15 pages total).
Iwabuchi et al., "Cyst fluid hemoglobin species in endometriosis and its malignant transformation: The role of metallobilogy", Oncology Letters, vol. 11, 2016, pp. 3384-3388. (6 pages total).

* cited by examiner

DATA ACQUISITION METHOD FOR DETERMINING LIKELIHOOD THAT OVARIAN ENDOMETRIOTIC CYST IS CANCEROUS, AND DIAGNOSTIC DEVICE FOR SAME

CROSS REFERENCE TO RELATED APPLICATIONS

This application is a National Stage of International Application No. PCT/JP2015/059693 filed Mar. 27, 2015, claiming priority based on Japanese Patent Application No. 2014-070166 filed Mar. 28, 2014, the contents of all of which are incorporated herein by reference in their entirety.

TECHNICAL FIELD

The present invention relates to a data acquisition method for determining likelihood or possibility of canceration or carcinogenesis of endometriosis ovarian cysts and a diagnostic device therefore.

BACKGROUND ART

Endometriosis is a common gynecological disease that occurs one woman in ten. Endometriosis ovarian cyst (benign ovarian cyst, called also as "chocolate cyst") is a kind of endometriosis and is a disease in which the endometriosis develop in the ovary and blood from the endometriosis accumulate to form a cyst.

It is reported that about 1% of the endometriosis ovarian cysts is cancerated into ovarian cancer ("endometriosis-associated ovarian cancer EAOC" which is a generic name of ovarian cancer that occurs from endometriosis). From epidemiological view point, if the cyst has a diameter of more than 6 cm and enlarges suddenly in a short period of time, extirpation is recommended for patients of 45 years old or older because of high risk of carcinogenesis.

However, it was reported a percentage of cases that are diagnosed as actual malignant tumor after surgery was only about 1%. In other words, a larger number of unnecessary invasive treatment were forced. Therefore, now, the likelihood of canceration is determined firstly by morphological evaluation of the cyst by using an ultrasonic diagnostic device or a nuclear magnetic resonance imaging (MRI).

Patent Document 1 discloses an ovarian cancer diagnose method by detecting overexpression of a specific biomarker that is selectively overexpressed in ovarian cancer.

Non-Patent Document 1 describes such a fact that the genetic factors that are believed to be involved in the development of endometriosis-associated ovarian cancer ("EAOC") are mutation of PTEN gene and strong expression of HNF-1 b gene or the like, while, in case of the endometriosis ovarian cysts, the concentration of free iron in the cyst fluid (using a production amount of lipid peroxide as an indicator) and an oxidative stress marker value become significantly higher comparing to other benign ovarian cysts, and hence the Non-Patent Document 1 suggests that a likelihood of accumulation of DNA damage which is caused by oxidative stress related to the free iron in the endometriosis ovarian cyst fluid and which lead to carcinogenesis in epithelial cells of endometriosis.

PRIOR ART DOCUMENTS

Patent Documents

Patent Document 1: JP-A1-2008-506123 (published Feb. 28, 2008)

Non-Patent Literature

Non-Patent Document 1: Masanori Bandai et al., Japan Society of Endometriosis Journal, Vol. 31, p. 65-69, 2010

SUMMARY OF THE INVENTION

Problems to be Solved by the Invention

However, it is difficult to distinguish actually between benign endometriosis ovarian cyst from cancerous endometriosis ovarian cyst by the morphological evaluation of cysts carried out by the ultrasonic diagnostic device or MRI. Therefore, in practice, a contrast agent is injected into the patient at the time of MRI imaging operation (contrast MRI test) to recognize cancerous parts. This test, however, imposes an excessive burden on a patient and can't be carried out in usual outpatient clinic.

In the method disclosed in Patent Document 1, it is impossible to determine whether or not the ovarian cancer is derived from endometriosis ovarian cyst. In fact, it is impossible to determine whether the endometriosis ovarian cyst is benign one or cancerous one by the method of Patent Document 1.

Up to today, the contrast MRI imaging method is only one established method for determining likelihood of canceration of endometriosis ovarian cyst. Many patients having endometriosis ovarian cysts undergo a surgical operation to remove the endometriosis ovarian cyst even though the cyst is not cancerous, taking into account a likelihood of future canceration.

On the other hand, the contrast MRI examination can't be carried out frequently, so that there is a danger that cancerous cases are missed. Precise judgement of whether or not the endometriosis ovarian cyst is actually cancerous can be done only by pathological examination of an extracted tissue.

The present invention was made in view of the above problems. An object of the present invention is to provide a method to acquire data that can be an indicative for determining a likelihood of canceration of endometriosis ovarian cyst.

Means for Solving the Problems

As mentioned above, there is a document reporting such a fact that accumulation of gene injury in epithelial cells of endometriosis caused by oxidative stress such as free iron of high concentration in the cyst liquid of endometriosis ovarian cyst will lead to carcinogenesis of the endometriosis ovarian cyst (such as Non-Patent Document 1).

The present inventors focuses on a relationship between the oxidative stress due to "iron" in the content liquid (hereinafter, "cyst fluid") of endometriosis ovarian cyst and a carcinogenesis mechanism of endometriosis ovarian cyst, and thought that it may be possible to determine a likelihood of canceration of endometriosis ovarian cyst by the iron concentration level in the cyst fluid. After intensive studies based on this hypothesis, the present inventors found firstly and surprisingly such a fact that the concentration of iron in the cyst fluid of a cancerous endometriosis ovarian cyst is significantly "lower" than the concentration of iron in the cyst fluid of the benign ovarian cyst. The present invention has been completed by this novel finding.

Thus, in order to solve the above problems, the present invention provides a method to acquire data which can be used for determining a likelihood of canceration of endometriosis ovarian cyst, including a measuring step for measuring the iron concentration in the cyst fluid of diseases ovarian cyst. The method according to the present invention is characterized in that the determination is made by any of following criterial (a) to (c):

(a) A likelihood of canceration is determined when the total iron concentration in the cyst fluid of the endometriosis ovarian cyst is higher than 0 mg/L and is equal to or less than 63 mg/L;
(b) a likelihood of canceration is determined when the heme iron concentration in the cyst fluid of the endometriosis ovarian cyst is higher than 0 mg/L and is equal to or less than 63 mg/L;
(c) A likelihood of canceration is determined when the free iron concentration in the cyst fluid of the endometriosis ovarian cyst is higher than 0 mg/L and is equal to or less than 10 mg/L.

The data acquisition method according to the present invention can include further a measuring step for measuring a met-heme/oxy-heme ratio in the cyst fluid of endometriosis ovarian cyst.

The present invention provides also a diagnostic device for diagnosing a likelihood of canceration of endometriosis ovarian cyst, characterized in that it comprises at least one measurement unit for measuring the iron concentration in the cystic fluid of endometriosis ovarian cyst.

In the diagnostic device according to the present invention, the measurement unit for measuring the iron concentration has a probe which can be inserted into the vagina of a subject.

The diagnostic device according to the present invention can include further a determination unit which can perform any of the following determinations (A) to (C):

(A) A likelihood of canceration of endometriosis ovarian cyst is determined when the concentration of the total iron in the cyst fluid is higher than 0 mg/L and equal to or less than 63 mg/L;
(B) A likelihood of canceration of endometriosis ovarian cyst is determined when the concentration of the heme iron in the cyst fluid is higher than 0 mg/L and equal to or less than 63 mg/L;
(C) A likelihood of canceration of endometriosis ovarian cyst is determined when the concentration of the free iron in the cyst fluid is higher than 0 mg/L and less equal to or than 10 mg/L.

In the diagnostic device according to the present invention, the measurement unit for measuring the iron concentration can be used to measure the ratio of met-heme/oxyheme in the cyst fluid of endometriosis ovarian cyst.

The diagnostic device according to the present invention can has an image forming unit for visualizing the endometriosis ovarian cysts.

In diagnostic device according to the present invention, a probe of the image forming unit can be arranged on an insertion member which can be inserted into the vagina of a subject.

In diagnostic device according to the present invention, the image forming unit ca be an ultrasound image forming unit.

The diagnostic device according to the present invention can have further a sampling or collecting part of the cystic fluid of endometriosis ovarian cysts.

Effect of the Invention

The data acquisition method according to the present invention permits to acquire data for determining a likelihood of canceration of endometriosis ovarian cysts by measuring the iron concentration in the cyst. Thus, it is possible to determine a likelihood of canceration of endometriosis ovarian cyst on the base of the data acquired by the data acquisition method according to the present invention. The possible of canceration of endometriosis ovarian cysts can be diagnosed by measuring the iron concentration in the cyst by the diagnostic device according to the present invention.

By the diagnostic device and data acquisition method according to the present invention, it is also possible to measure the iron concentration in the cyst on in real-time by using a non-restricted, painless and non-invasive method. Therefore, the data acquisition method and the diagnosis apparatus according to the present invention contribute highly to the clinical practice.

It should be noted that the above method is used only for determine a likelihood of canceration of endometriosis ovarian cysts, but is not a definitive diagnosis method to know whether or not the endometriosis ovarian cyst is cancerous. The definitive diagnosis to know whether the endometriosis ovarian cysts are cancerous or not must be performed by histopathological diagnoses.

BRIEF DESCRIPTION OF DRAWINGS

FIG. 6 (a) is an illustrative drawing showing a structure of a probe of an iron concentration measurement unit of the diagnostic device according to embodiments of the present invention, and (b) and (c) are illustrative drawings showing structures of probe and image forming portion of iron concentration measurement units of the diagnostic device according to embodiments of the present invention,

DESCRIPTION OF THE INVENTION

Now, the present invention will be described in details with referring to embodiments of the present invention. The present invention is not limited to the embodiments but can be modified within the scope of invention defined in the claims. All the academic publications and patent documents cited herein are incorporated by reference herein. A numerical range expressed by "A to B" means "more than A and less than B" (end included) unless otherwise stated.

1. Data Acquisition Method

The data acquisition method according to the present invention (hereinafter, "data acquisition method of the present invention") is a method for acquiring data which is used to determine a likelihood of canceration of endometriosis ovarian cyst and includes at least a step of measuring the concentration of iron in the cyst fluid in the endometriosis ovarian cyst ("iron concentration measuring step").

The data acquisition method according to the present invention can be carried out by any steps and is not limited particularly, provided that it contains the iron concentration measuring step for measuring the iron concentration in cystic fluid of endometriosis ovarian cysts. Determination step which is effected by doctor or physician is not included in the data acquisition method of the present invention.

The doctor or physician can determine a likelihood of canceration of endometriosis ovarian cysts on the base of the data acquired by the data acquisition method of the present invention. In practice, the determination is made by at least one of following criterial (a) to (c):

(a) A likelihood of canceration of endometriosis ovarian cysts is determined when the total iron concentration in the cyst fluid is not lower than 0 mg/L and equal to or less than 63 mg/L;
(b) A likelihood of canceration of endometriosis ovarian cysts is determined when the heme iron concentration in the cyst fluid is not lower than 0 mg/L and equal to or less than 63 mg/L;
(c) A likelihood of canceration of endometriosis ovarian cysts is determined when the free iron concentration in the cyst fluid is not lower than 0 mg/L and equal to or less than 10 mg/L.

Above judgment or criterial is based on such unexpected finding that the iron concentration in the cyst fluid of cancerous endometriosis ovarian cyst is significantly "lower" than that of benign endometriosis ovarian cyst. This finding was made firstly by the present inventors.

A mechanism associated with this finding is unknown but the present inventors think that following is a reason why the iron concentration of cancerous endometriosis ovarian cysts is "lower" than that of benign endometriosis ovarian cysts: In fact, usually, most cells of the endometriosis will die before they become cancerous or canceration or oncogenesis because the concentration of iron in the cystic fluid is high. On the contrary, when cells of the endometriosis produce a detoxification enzyme against oxidative stress and hence the ability to treat irons of the cells of endometriosis is enhanced (in this case, the iron concentration in the cystic fluid become lower), the cells of endometriosis don't die but continue survival with maintaining the genetic instability until final canceration.

The data acquisition method according to the present invention is applicable to subjects or patients having endometriosis ovarian cysts. The subjects are not limited to human being but can be any living organisms that will develop the endometriosis ovarian cysts and may be mammals in general.

1-1. Iron Concentration Measuring Step

The iron concentration measuring step is a step for measuring iron concentration in the cyst fluid of endometriosis ovarian cysts. The method for measuring the iron concentration in cystic fluid of endometriosis ovarian cysts used in the iron concentration measurement step is not limited to specific method bur can be any method as long as the iron concentration in cystic fluid can be measured.

The "cyst fluid of endometriosis ovarian cyst" means a liquid accumulated in the endometriosis ovarian cyst. The "measuring of the iron concentration in cystic fluid cyst fluid" can be carried out "in vitro" in which a sample of the cystic fluid is collected from a subject having endometriosis ovarian cysts to measure the iron concentration in the cyst fluid, or "in vivo" in which the iron concentration in cystic fluid is measured under such a condition that the cyst fluid is encapsulated in endometriosis ovarian cyst of the subject.

"Iron" that is measured in the iron concentration measurement step can be at least one member selected from the group consisting of the total iron, the heme iron and the free iron (non-heme iron).

"Total iron" refers to all of iron atoms that are present in the cyst fluid. The total iron concentration of cystic liquid can be measured by any known method but is not is not limited to a specific method as long as the total iron concentration can be measured. Known methods for measuring the total iron concentration in cystic fluid "in vitro" are, for example, the total iron concentration of cystic liquid can be measured by ICP (inductively-coupled plasma:inductively coupled plasma) optical emission spectrometry method which is used in Examples described below (See Analytical Techniques for Clinical Chemistry, methods and Applications, p 281-283 John Wiley & Sons, Inc, 2012, ISBN: 1118271831, 9781118271834) and ICP mass spectrometry method.

The "heme iron" refers to iron atoms forming a porphyrin complexes in the heme. When the "heme" is "met-heme", the "heme iron" refers to a trivalent iron ion ($Fe^{3+}$) in which oxygen as axial ligand is not bound. When the "heme" is "oxy-heme", the "heme iron" refers to a divalent iron ion ($Fe^{2+}$) in which oxygen as axial ligand is bound. Thus, the "heme iron concentration" measured in the iron concentration measurement step is the sum of the concentrations of the trivalent iron ion ($Fe^{3+}$) and of the divalent iron ions ($Fe^{2+}$). Hemoglobin comprises the heme iron (iron porphyrin complex) and globin (protein).

Method to measure the heme iron concentration in cystic fluid is not limited specially and can be any method as long as the heme iron concentration can be measured. Known method to measure the heme total iron concentration in the cyst fluid in the in vitro is, for example, Triton-MeOH assay chromogenic method used in Examples which will be described later (See A V Pandey, S K Joshi, B L Tekwani, & V. S., Chauhan, Anal Biochem 268 (1999) P. 159) and High performance liquid chromatography method (See. J D Weinstein & S I Beale, J. Biol Chem 258 (1983) P6799).

The "free iron" refers to iron atoms that do not form the porphyrin complex or irons which are not heme irons (non-heme iron) among chemical species associated with irons in the body. Method to measure the free iron concentration in cystic fluid is not limited specially and can be any method as long as the free iron concentration can be measured. Known method to measure the free iron concentration in the cystic fluid in vitro is, for example, chelating chromogenic method used in Examples which will be described later (See Hiroko Suzuki, Toru Otsuki, Natsuki Ito, Bunpei Sato, Koide Kazuhiro, Takuya Iwabuchi, Saibou 46 (1), 2014 and Mikihiko Saito, Daikichi Horiguchi, Kina Kenlsamu, Bunseki Kagaku, 30,635-639 (1981)).

When the cyst fluid is contained in endometriosis ovarian cysts of a subject, the iron concentration of iron in the cyst fluid can be measured in vivo, for example, by known methods such as near-infrared spectroscopy, nuclear magnetic resonance spectroscopy (MRS), neutron activation analysis and X-ray fluorescence analysis. Thus, the iron concentration in the cyst fluid can be measured nondestructively by using these methods. The near-infrared spectroscopy can be a reflection type or a transmission type.

1-2. Presence Ratio Measuring Step

The data acquisition method according to the present invention can include further a step to measure a presence ratio for determining the presence ratio (concentration ratio or sensitivity ratio which will be described later) of met-heme/oxy-heme in the cyst fluid of the endometriosis ovarian cyst. As mentioned above, the "heme iron" refers to a trivalent iron ions (Fe3+) in which oxygen is not bound as axial ligand, while "heme iron" refers to a divalent iron ion (Fe2+) in which oxygen is bound as axial ligand when the "heme" is "oxy-heme".

As shown in Example 2 described later, the present inventors revealed such a fact that the main composition of a cyst fluid of benign endometriosis ovarian cysts (benign ovarian cyst) is "met-heme", while the primary composition of a cyst fluid of cancerous or oncogenesis endometriosis ovarian cysts is "oxy-heme". Based on this new knowledge, we can be determined that the cyst is non-cancer when the iron concentration in the cyst is Fe3+predominant (Fe3+>Fe2+), and the cyst is cancer when the iron concentration in the cyst is Fe2+predominant (Fe2+>Fe3+). In other words, a likelihood of canceration or cancerous state of the endometriosis ovarian cyst can be determined if the ratio of concentration of met-heme/oxy-heme in cyst fluid is lower than 1/1.

Thus, another high precision indicator which can be used for determining a likelihood of canceration of endometriosis ovarian cyst can be obtained by measuring the concentration ratio of met-heme/oxy-heme in cyst fluid of endometriosis ovarian cyst.

The met-heme concentration and oxy-heme concentration in the cyst fluid can be determined by electronic absorption spectra as shown in Example 2. More precisely, for example, a sample of the cyst fluid is irradiated by ultraviolet or visible light and transmitted light (or reflected light) is observed in term of absorbance. It is possible to estimate the presence ratio of met-heme and oxy-heme (concentration ratio) from a difference because there is a typical difference in spectral shapes of the met-heme and of oxy-heme.

It is possible to measure the concentration of trivalent iron ions (Fe3+) constituting the met-heme and the concentration of divalent iron ion (Fe2+) constituting oxy-heme in the cystic fluid, instead of measuring the concentrations of met-heme and of oxy-heme. In this case, obtained measured values are converted into the met-heme concentration and the oxy-heme concentration respectively, so that the resulting conversion values can be used as indicators for determining a likelihood of canceration of endometriosis ovarian cysts.

In the present invention, the presence ratio of met-heme/oxy-heme in the cyst fluid can be measured also by measuring the sensitivity of wavelength (absorbance (ABS) or optical density (O.D)) to which met-heme and oxy-heme attribute respectively, and calculating a sensitivity ratio of the sensitivities obtained. For example, as is described later in Example 5, a wavelength of 580 nm is selected as a marker wavelength for oxy-heme and a wavelength of 620 nm is selected as a marker wavelengths for met-heme respectively and a sensitivity ratio (=O.D 620 nm/O.D 580 nm) is calculated from measured sensitivities obtained. A likelihood of canceration of the endometriosis ovarian cyst can be determined from the sensitivity ratio. In fact, the endometriosis ovarian cyst is not cancerous (benign ovarian cyst) when the sensitivity ratio is not lower than 0.5. On the contrary, the sensitivity ratio is higher than 0 and equal to or less than 0.5, canceration or carcinogenesis or oncogenesis is determined.

It should be noted that the marker wavelength of met-heme/oxy-heme is not limited to the above 620 nm/580 nm adopted in Example 5, but other suitable wavelengths that attribute to met-heme and oxy-heme respectively can be used in the present invention. For example, a marker wavelength for the met-heme can be selected in the vicinities of 400 nm, 490 nm and 620 nm respectively. A marker wavelength for the oxy-heme can be selected in the vicinities of 415 nm (Soret band), 545 nm (β band) and 570 nm (α band) respectively. Term "in the vicinity" means the maximum wavelength±20 nm. In practice, the sensitivity of each wavelength (absorbance or optical density) in the cyst fluid samples are measured to obtain the sensitivity ratios. Since there is a significant difference in the sensitivity ratio between the cancer group and the non-cancer group, a threshold value between cancer and non-cancer can be calculated or set from the average value of the sensitivity ratio of the cancer group and the average value of the sensitivity ratio of non-cancer group. The threshold value can be determined by the method carried out in Example 5.

By using the data acquisition method according to the present invention, patients having endometriosis ovarian cysts can determine in advance whether or not surgical treatment for removing the endometriosis ovarian cysts before the surgical treatment is actually effected. Heretofore, many of patients having endometriosis ovarian cysts undergone surgical treatment to remove the ovarian cyst, although many patients are not cancerous, with taking into account the likelihood of endometriosis ovarian cyst is cancerous. Therefore, unnecessary surgery can be reduced by using the data acquisition method according to the present invention, resulting in that patient's burden can be reduced.

Furthermore, the data acquisition method according to the present invention permits to measure the iron concentration in the endometriosis ovarian cysts real-time, non-binding and nondestructively, so that determination of likelihood that an endometriosis ovarian cyst is cancerous can be realized real-time with non-binding and non-destructive manner. In fact, the iron concentration in cyst fluid can be measured real-time, non-binding, non-destructive manner by measuring the total iron concentration in cystic fluid by using known method such as near-infrared spectroscopy and visible spectroscopy. As a result, it becomes possible to follow-up regularly outpatient having endometriosis ovarian cysts, so that canceration of endometriosis ovarian cysts can be discovered at early stage.

The data acquisition method according to the present invention can be combined with a method for determining a likelihood that endometriosis ovarian cysts are cancerous which is carried out by a device or physician. The method including the step for determining the likelihood that endometriosis ovarian cysts is performed by at least one of following determination or criteria (a) to (c):

(a) Likelihood that the endometriosis ovarian cyst is cancerous is determined when the total iron concentration of the cyst fluid is higher than 0 mg/L and equal to or less than 63 mg/L;

(b) Likelihood that the endometriosis ovarian cyst is cancerous is determined when the hem iron concentration of the cyst fluid is higher than 0 mg/L and equal to or less than 63 mg/L;
(c) Likelihood that the endometriosis ovarian cyst is cancerous is determined when the free iron concentration of the cyst fluid is higher than 0 mg/L and equal to or less than 10 mg/L;

2. Diagnostic Device

The diagnostic device according to the present invention ("diagnostic device of the present invention") is a diagnostic device for diagnosing a likelihood that the endometriosis ovarian cyst is cancerous and is equipped with at least an iron concentration measurement unit for measuring the iron concentration in the cyst fluid of endometriosis ovarian cysts, by a near infrared spectroscope for example. Structure other than the above iron concentration measurement unit in the diagnostic device according to the present invention is not limited specially and can have any configuration and may have an image-forming unit which will be described below.

2-1. Iron Concentration Measuring Unit

The iron concentration measurement unit is not limited to special ones as long as the iron concentration in cystic fluid can be measured. The iron concentration measurement unit can be configured in such a manner that the method of measuring the concentration of iron in the cystic fluid according to the present invention can be carried out real-time, under non-restricted, painless and non-invasive manner (for example, by a well-known near-infrared spectroscopy, visible spectroscopy, etc.). For example, the iron concentration measurement unit has at least a probe that emits and receives infrared light, and a data processing unit for calculating the concentration of iron in the cystic fluid from an absorption spectrum of near-infrared light obtained.

The "probe" may has at least a light emitting part that emits near-infrared light and a light receiving part for receiving a near infrared light reflected from the cystic fluid or a near infrared light transmitted through the cystic fluid. Method for measuring the near-infrared light of spectroscopy is not limited to specific ones but can be a reflection type or a transmission type. The reflective type near infrared spectroscopy is preferably to measure the iron concentration in the cystic fluid, since the light emitting part and the light receiving part can be located at close proximity in an iron concentration measurement unit. In case of the transmission type infrared spectroscopy, a light receiving part must be positioned at a position which can receive a near infrared light transmitted through the cyst fluid. However, it is not so easy to position the light-receiving portion in a body. Therefore, it is preferable to use the reflective type near infrared spectroscopy to measure the iron concentration in the cystic fluid.

In the present invention, the iron concentration of the cyst fluid of endometriosis ovarian cysts can be measured non-destructively in vivo by the near-infrared spectroscopy under such a condition that the cyst fluid is encapsulated in the endometriosis ovarian cyst of a subject.

The "iron" that is measured in the iron concentration measurement unit can be at least one selected from the group consisting of heme iron, total iron and free iron. Details of the total iron, heme iron and free iron are described in "1. Data acquisition method" and hence their explanation is omitted here.

Since the total iron concentration in the cystic fluid is approximate to the concentration of hemoglobin, the total iron concentration in the cystic fluid can be determined by the method for determining the quantity of hemoglobin by near-infrared spectroscopy. The heme iron concentration in the cystic fluid can be determined by the method for determining the quantity of hemoglobin by near-infrared spectroscopy, since the heme iron concentration in the cystic fluid is approximate to the concentration of hemoglobin. When the concentration of the free iron in cystic fluid is measuring by a near-infrared spectroscopy, the quantitative analysis can be performed by spectrometric determination by using a ferrous selectively chelate compound having a functional group containing chromophore and auxochrome to the near-infrared wavelength.

Figure 6:
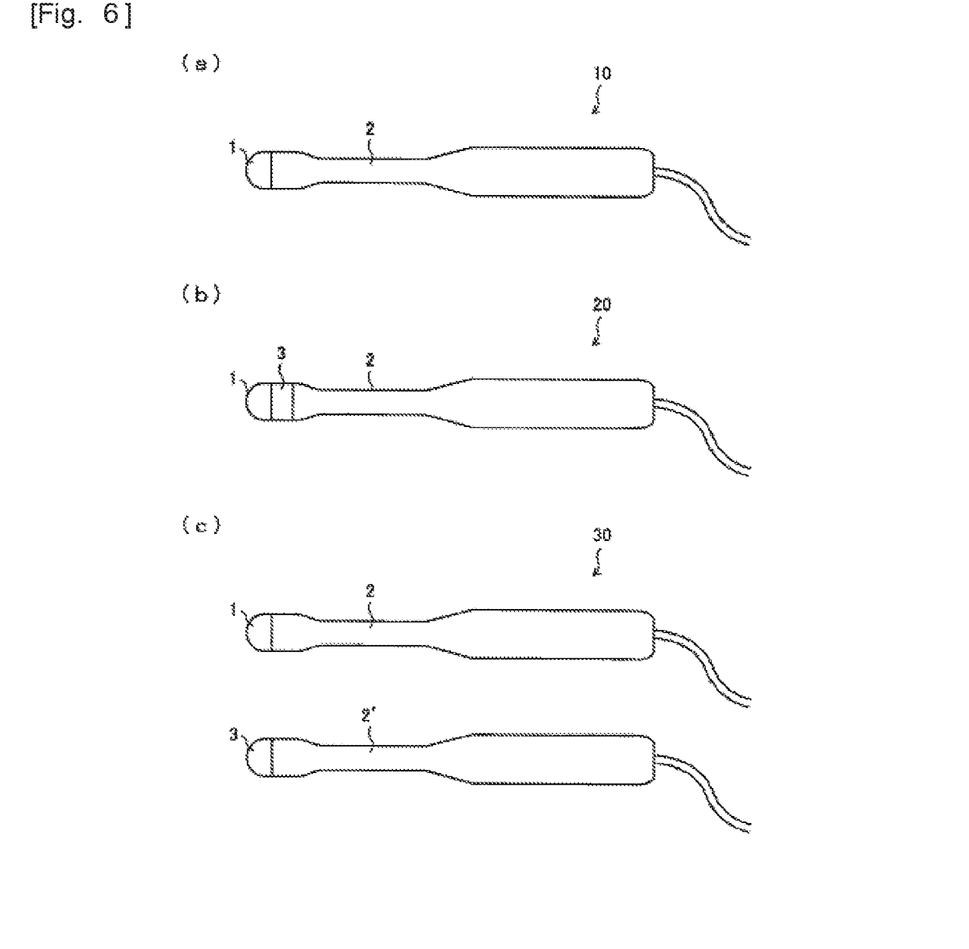

FIG. 6 (a) is an illustrative drawing showing a configuration of a probe 1 of the iron concentration measurement unit of the diagnostic device 10 according to an embodiment of the present invention. In the diagnostic device of the present invention, the probe 1 of the iron concentration measurement unit is positioned preferably in the vicinity of the tip portion of an insertion member 2 which can be inserted into the vagina of a subject. The probe can be inserted to the vicinity of endometriosis ovarian cysts, so that the iron concentration in the cyst of endometriosis ovarian cysts can be measured at higher sensitivity.

The diagnostic device 10 can be provided with a sampling tool for collecting a cyst fluid of endometriosis ovarian cysts (tool for liquid biopsy, etc.), and also may be contained reagent(s) for measuring the iron concentration in the cyst fluid collected and a judgment program or the like which permit real time measurement and determination of the iron concentration. Alternately, the measurement and determination of the iron concentration can be carried out remotely by using an external computer and electronics devices. The sampling tool can be integrated with the insertion member or separated from the insertion member to form a separate body.

Material, shape, size, structure of the "insertion member" are not limited especially as long as the probe of the iron concentration measurement unit can be inserted into the vagina of a subject. For example, an insertion member for a probe of an ultrasonic diagnostic device which is generally used in transvaginal ultrasonography can be used as the insert member for the probe of the iron concentration measurement unit in the present invention.

In the diagnostic device according to the present invention, the presence ratio of met-heme/oxy-heme in the cyst fluid of endometriosis ovarian cysts (concentration ratio or sensitivity ratio) can be measured by the iron concentration measurement unit. As explained in "1. Data acquisition method", a likelihood that the endometriosis ovarian cyst is cancerous can be determined when the concentration ratio of met-heme/oxy-heme is lower than 1/1. As explained in "1. Data acquisition method", the presence ratio of met-heme/oxy-heme in cyst fluid can be measured also by measuring the sensitivity (absorbance (ABS) or optical density (O.D)) of met-heme and oxy-heme at attributed wavelengths to calculate a ratio of their sensitivities.

The likelihood that endometriosis ovarian cyst is cancerous can be diagnosed at a higher degree of accuracy by determining the presence ratio of met-heme/oxy-heme in cyst fluid of endometriosis ovarian cysts by using the iron concentration measurement unit.

2-2. Determination Unit

The diagnostic device according to the present invention can have further a determination (diagnosis) unit for judging the likelihood that endometriosis ovarian cyst is cancerous by using cut-off value which was input or stored previously in the diagnostic device.

The determination (diagnosis) unit diagnoses the likelihood according to one of following criteria (A) to (C):
(A) Likelihood that the endometriosis ovarian cyst is cancerous is determined when the total iron concentration of the cyst fluid is higher than 0 mg/L and equal to or less than 63 mg/L;
(B) Likelihood that the endometriosis ovarian cyst is cancerous is determined when the hem iron concentration of the cyst fluid is higher than 0 mg/L and equal to or less than 63 mg/L;
(C) Likelihood that the endometriosis ovarian cyst is cancerous is determined when the free iron concentration of the cyst fluid is higher than 0 mg/L and equal to or less than 10 mg/L;

The cut-off value is a value which divides positive and negative in the quantitative test. The cut-off value is different from a reference range but is a value which separates a patients group suffering from a particular disease from a non-patient group. In other words, the reference range is a unique value to an inspection item, while the cut-off value is a specific value to a pair of an inspection item and disease (group).

Since the diagnostic device according to the present invention has the determination unit, it is possible to diagnose automatically a likelihood that endometriosis ovarian cyst is cancerous, so that determination of cancer or not can be performed easily.

The determination unit can determine also following (D) and (E) in addition to the above (A) to (C):
(D) There is a likelihood that endometriosis ovarian cyst is cancerous; when the concentration ratio of met-heme/oxy-heme in the cyst fluid is lower than 1/1.
(E) Likelihood that endometriosis ovarian cyst is cancerous is determined on the base of the threshold of a sensitivity ratio (=the sensitivity of a marker wavelength for met-heme/the sensitivity of a marker wavelength for oxy-heme). For example, likelihood that endometriosis ovarian cyst is cancerous is determined when a sensitivity ratio (=O.D 620 nm/O.D 580 nm) is higher than 0 and equal to or less than 0.5. On the contrary, it is determined that endometriosis ovarian cyst is not cancerous when the sensitivity ratio is higher than 0.5.

2-3. The Image Forming Unit

The diagnosis device according to the present invention can have further an image forming unit for visualizing endometriosis ovarian cysts, so that measurement of the iron concentration in the cyst fluid of endometriosis ovarian cyst can be carried out while confirming a position of the endometriosis ovarian cysts of interest for diagnosing tumor in the image. It is also possible to sampling a cyst fluid (liquid biopsy) by providing a sampling tool for collecting the cyst fluid of endometriosis ovarian cysts to the diagnostic device, while confirming the target position in the image.

Confirmation of whether the subject has endometriosis ovarian cysts or not (screening of endometriosis ovarian cyst patients) and of measurement of the iron concentration in the cyst fluid of endometriosis ovarian cysts (determination of a possibility of likelihood that endometriosis ovarian cysts are cancerous) when the presence of endometriosis ovarian cyst is observed or confirmed can be performed efficiently.

The image forming unit according to the present invention can be any type as long as endometriosis ovarian cysts of interest for diagnosing cancerous can be visualized and is not limited to special ones. The image forming unit can have the same configuration or structure as an ultrasonic diagnostic device which is used commonly in ultrasound diagnosis in the medical field, X-rays imaging apparatus, CT (computerized tomography) imaging apparatus and MRI diagnosis apparatus. The ultrasonic diagnostic device (=ultrasonic imaging unit) can be used preferably as the image forming unit. The ultrasonic diagnostic device can be for example an extracorporeal ultrasonic diagnostic device used in abdominal ultrasonography from a body surface, or an ultrasonic diagnostic device used in transvaginal ultrasonography.

The probe of the image forming unit of the diagnostic device according to the present invention is preferably arranged on an insertion member which can be inserted into the vagina of a subject, so that the probe can be inserted up to the vicinity of endometriosis ovarian cysts and the endometriosis ovarian cysts can be visualized more sensitively. The image forming unit can be an ultrasonic diagnostic device used in transvaginal ultrasonography and the probe of the image forming unit can be a probe used in transvaginal ultrasonography.

FIGS. 6 (*b*) and (*c*) are schematic views of another embodiments of the diagnostic device according to the present invention and show a probe 1 for measuring the iron concentration in a diagnosis device 20 and a probe 3 of an image forming unit and in a diagnosis device 30 respectively. The probe 1 for measuring the iron concentration and the probe 3 of the image forming unit can be integrated in a single insertion member 2 (in FIG. 6 (*b*)) or can be arranged independently on respective separate insertion member 2 and 2' (FIG. 6 (*c*)). Both of the probe 1 for measuring the iron concentration and of the probe 3 for the image forming unit are preferably integrated so that both probes can be inserted simultaneously intravaginally to improve handling properties of the device Material, shape, size and structure of the "insertion member" are not particularly limited but can be any ones as long as the probe of the image forming unit can be inserted into the vagina of a subject. It is possible to use those used in insertion members for the probes of the ultrasonic diagnostic device which are commonly used in transvaginal ultrasonography.

By using the diagnostic device according to the present invention for the patients having endometriosis ovarian cysts, likelihood that endometriosis ovarian cysts are cancerous can be determined, so that whether surgical treatment to remove the endometriosis ovarian cysts should be done or not can be decided in advance or in real time before the endometriosis ovarian cysts are actually removed by surgical treatment. Thus, it is possible to reduce unnecessary surgery, resulting in that t it is possible to reduce advantageously a patient's burden.

Furthermore, likelihood of endometriosis ovarian cysts are cancerous can be seen or determined in real time by using the diagnostic device according to the present invention, so that it is possible to enter the next surgical procedure quickly when a high likelihood of cancer is determined by the iron concentration measurement of a sample collected by biopsy or liquid biopsy.

Stillmore, the iron concentration in the cyst can be measured non-destructively by using the diagnostic device according to the present invention, and likelihood that endometriosis ovarian cysts are cancerous can be diagnosed non-destructively. Therefore, it is possible to follow-up outpatient having endometriosis ovarian cysts regularly, so that patient's canceration of endometriosis ovarian cysts can be discovered in an early stage.

The data acquisition method according to the present invention can be carried out by using the diagnostic device according to the present invention.

The present invention is not limited to the embodiments described above but covers a variety of embodiments which fall within the scope of claims. Combinations of technical means disclosed in different embodiments also covered by the scope of the present invention.

EXAMPLES

Hereinafter, the present invention is described with referring Examples, but the present invention is not limited by following examples.

Example 1

The total iron concentration in the cystic fluid was measured by inductively coupled plasma (ICP) emission spectrometry by using samples of cyst fluids of endometriosis ovarian cysts ("endometriosis cyst" or "endometrial cyst") as specimens. ICP analysis device used was Vista-MPX-type analyzers manufactured by Varian.

Results of measurement are summarized in Table 1.

TABLE 1

| Case | | Clinical diagnosis | Total iron density (mg/L) |
|---|---|---|---|
| A | 1 | Endometrioid adenocarcinoma | 30 |
|   | 2 | Right endometrial cyst | 621 |
| B | 1 | Left endometrial cyst ruptured | 449 |
|   | 2 | Right endometrial cyst non-ruptured | 291 |
| C |   | Left endometrial cyst | 202 |
| D |   | Left endometrial cyst | 548 |
| E |   | Undifferentiated cancer | 11.85 |
| F |   | Left endometrial cyst | 67.15 |
| G | 1 | Right endometrial cyst | 315.2 |
|   | 2 | Left endometrial cyst | 205.0 |
| H | 1 | Left endometrial cyst | 65.3 |
|   | 2 | Right endometrial cyst | 300.3 |
| I |   | Left endometrial cyst | 322.5 |
| J |   | Right endometrial cyst | 230.1 |
| K |   | Left endometrial cyst | 78.4 |
| L |   | Right endometrial cyst | 1048.3 |
| M |   | Left endometrial cyst | 327.6 |
| N |   | Clear cell adenocarcinoma | 39.0 |
| O |   | Left endometrial cyst | 316.3 |
| P |   | Right endometrial cyst | 163.8 |

Results of measurement of the total iron concentration in cyst fluid revealed such a fact that the total iron concentration for a group whose uterine endometriosis ovarian cysts is cancerous (referred to as "cancer group" in which ovarian cancer is developed) is relatively lower than a group whose uterine endometriosis ovarian cysts is not cancerous (hereinafter referred to as "non-cancer group" in which ovarian cancer is benign).

Figure 1:
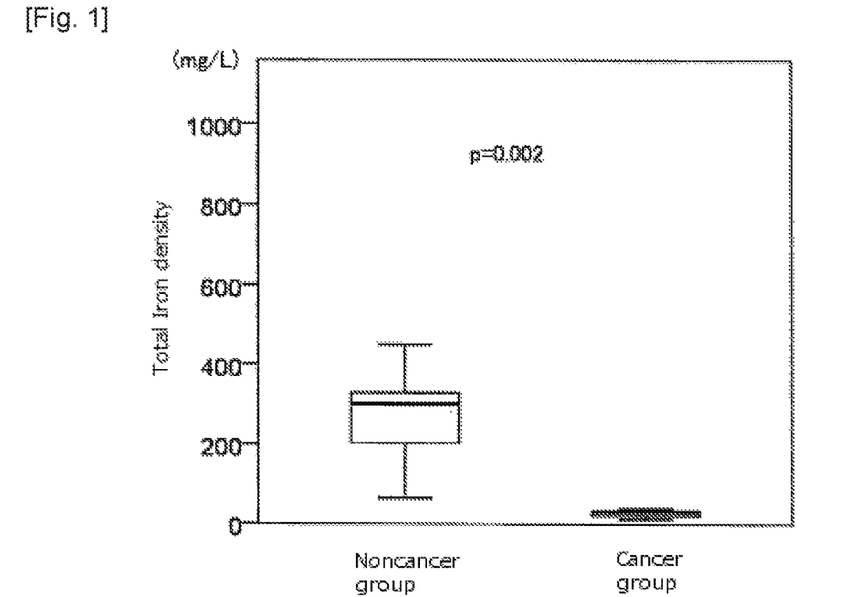
FIG. 1 is a graph showing the results of a difference in the average values of the concentration of total iron in the cystic fluid between endometriosis ovarian cyst group (hereinafter, non-cancer group) and a group in which the endometriosis ovarian cyst became to ovarian cancer (hereinafter cancer group), tested by non-parametric analysis (Mann-Whitney U-test).

FIG. 1 shows the results of a difference between an average value of the total iron concentration in the cancer group and an average value of the total iron concentration in the non-cancer group and verified by non-parametric analysis (Mann-Whitney U-test). The results reveal such a fact that there is a significant difference between the average value of the total iron concentration in the cancer group (=26.95 mg/L) and the average value of the total iron concentration in the non-cancer group (=326.2 mg/L) ($p=0.002$).

The above results show that it is possible to determination a likelihood that endometriosis ovarian cysts are cancerous by measuring the total iron concentration in cystic fluid as an indicator.

Example 2

Electronic absorption spectrum was measured to clarify a difference between a composition of the cyst fluid of benign ovarian cysts and a composition of the cyst fluid of cancerous endometriosis ovarian cysts.

Each cyst fluid was dispensed into wells and the electron absorption spectrum was measured by a microplate reader (CORONA Ltd., SH-1200).

Figure 2:
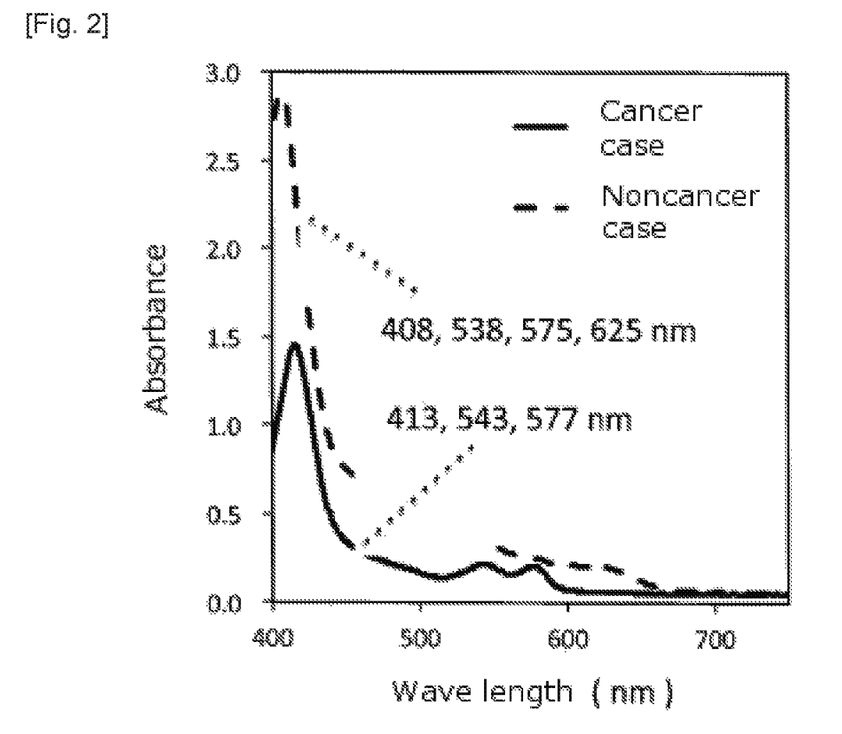
FIG. 2 is a graph showing the results of electric absorption spectra of the cystic fluid measured in the non-cancer group and cancer group.

FIG. 2 shows the results of measurement. The electronic absorption spectra for the cyst fluid of non-cancer group show the absorption maxima at 408 nm, 538 nm, at 575 nm and 625 nm. On the other hand, the electronic absorption spectra for the cyst fluid of non-cancer group show the absorption maxima at 412 nm, 543 nm and 577 nm. From these spectra, it was found that the primary composition of the cyst fluid of non-cancer group is met-heme. On the other hand, the primary composition of the cyst fluid of the cancer group is oxy-heme.

Example 3

From the results of Example 2, it was speculated that the main composition of cyst fluid of endometriosis ovarian cysts is iron from heme (heme iron). Therefore, an amount of heme iron contained in the cyst fluid of endometriosis ovarian cysts is measured quantitatively to know more detailed composition of the cyst fluid.

The content of heme iron was quantified by Triton-MeOH assay coloring method by using the cyst fluid of cancer group and non-cancer group as specimen in the same manner as in Example 1. Quantification Kit used was a metalloproteinase assay LS heme assay kit (manufactured by Metallogenics Co., Ltd.). Electronic absorption spectrum was measured by a microplate reader (CORONA, SH-1200 type).

The measurement results are shown in Table 2.

TABLE 2

| Case | | Clinical diagnosis | Heme-originated iron density (mg/L) |
|---|---|---|---|
| A | 1 | Endometrioid adenocarcinoma | 25 |
|   | 2 | Right endometrial cyst | 467 |
| B | 1 | Left endometrial cyst ruptured | 283 |
|   | 2 | Right endometrial cyst non-ruptured | 196 |
| C |   | Left endometrial cyst | 138 |
| D |   | Left endometrial cyst | 604 |
| E | 1 | Right endometrial cyst | 124 |
|   | 2 | Left endometrial cyst | 237 |
| F | 1 | Left endometrial cyst | 93 |
|   | 2 | Right endometrial cyst | 402 |
| G |   | Left endometrial cyst | 374 |
| H |   | Right endometrial cyst | 305 |
| I |   | Left endometrial cyst | 93 |
| J |   | Right endometrial cyst | 758 |
| K |   | Left endometrial cyst | 304 |
| L |   | Clear cell adenocarcinoma | 62.3 |
| M |   | Left endometrial cyst | 534 |
| N |   | Right endometrial cyst | 563 |

Differences between an average value of the heme iron concentration of cyst fluid in the cancer group and an average value of the heme iron concentration of cyst fluid in the non-cancer group were assayed by parametric analysis (U-test of Mann-Whitney) in the same manner as in Example 1. The results are shown in FIG. 3.

Figure 3:
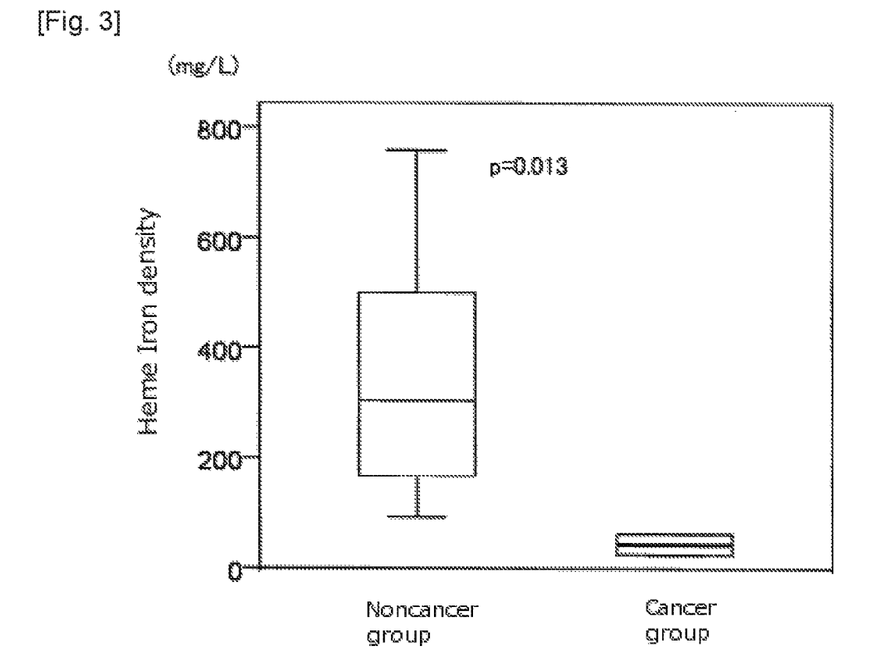
FIG. 3 is a graph showing the results of a difference in the average values of the concentration of heme iron in the cystic fluid between, non-cancer group and cancer group, tested by non-parametric analysis (Mann-Whitney U-test).

From the results shown in FIG. 3, it is revealed that the total iron concentration and the heme iron concentration in the cyst fluid are almost identical in case of the non-cancer group. Therefore, it is found that primary composition of the cyst fluid of endometriosis ovarian cysts is heme iron originated from the blood.

Furthermore, there is a significant difference between the mean value of the heme iron concentration among groups (cancer group=43.63 mg/L, non-cancer group=342.19 mg/L) (p=0.013).

Therefore, like the results of Example 1, it is confirmed that likelihood that endometriosis ovarian cysts are cancerous can be determined by using the concentration of heme iron in cystic fluid as an indicator.

The results of Examples 1 and 3 show such a fact that the maximum value of the total iron concentration or of heme iron concentration in the cyst fluid of cancer group was 62.3 mg/L (cases L in Table 2), while the minimum value of the total iron concentration or of heme iron concentration in non-cancer group was 65.3 mg/L (cases of H1 in Table 1).

From this fact, the inventors concluded that we can judge or determine likelihood that endometriosis ovarian cysts are cancerous as following: the endometriosis ovarian cysts may not be cancerous (there is a likelihood of benign ovarian cyst) when the total iron concentration or the heme iron concentration in cystic fluid is 63 mg/L or more, while the endometriosis ovarian cysts may cancerous when the heme iron concentration in cystic fluid is higher than 0 mg/L and equal to or less than 63 mg/L.

Since the total iron concentration is almost same as the heme iron concentration in the cyst fluid of endometriosis ovarian cysts, it is possible to measure the concentration of heme, instead of measuring the heme iron concentration in cystic fluid, and the iron concentration is calculated or converted from a measured value. Thus, the converted value can be used as an indicator to determine likelihood that endometriosis ovarian cyst is cancerous.

Example 4

From Example 3, it became clear that the main composition in the cyst fluid of endometriosis ovarian cysts is heme iron. However, there is also free iron as non-heme iron as chemical species associated with irons in the body. Heretofore, chemical species of irons contained in the cyst fluid were unknown. Therefore, we measure quantitatively the free iron content in the cyst fluid.

The concentration of free iron was determined by the chelating coloring method in the same manner as in Example 1 by using the cyst fluid of endometriosis ovarian cysts as a specimen. Quantitative determination kit used was a metallo assay iron measurement kit LS (product of Metallogenics Co., Ltd.) and the electronic absorption spectrum was measured by a microplate reader (CORONA, SH-1200 type).

The measurement results are shown in Table 3.

TABLE 3

| Case | | Clinical diagnosis | Free iron density (mg/L) |
|---|---|---|---|
| A | 1 | Endometrioid adenocarcinoma | 4.5 |
|   | 2 | Right endometrial cyst | 32.2 |
| B | 1 | Left endometrial cyst ruptured | 16.7 |
|   | 2 | Right endometrial cyst non-ruptured | 12.0 |
| C |   | Left endometrial cyst | 12.9 |
| D |   | Left endometrial cyst | 13.5 |
| E |   | Undifferentiated cancer | 3.1 |
| F |   | Left endometrial cyst | 11.0 |
| G | 1 | Right endometrial cyst | 19.0 |

TABLE 3-continued

| Case | | Clinical diagnosis | Free iron density (mg/L) |
|---|---|---|---|
|   | 2 | Left endometrial cyst | 16.7 |
| H | 1 | Left endometrial cyst | 14.3 |
|   | 2 | Right endometrial cyst | 16.7 |
| I |   | Left endometrial cyst | 33.3 |
| J |   | Right endometrial cyst | 23.8 |
| K |   | Left endometrial cyst | 11.9 |
| L |   | Right endometrial cyst | 92.9 |
| M |   | Left endometrial cyst | 33.3 |
| N |   | Clear cell adenocarcinoma | 7.1 |
| O |   | Left endometrial cyst | 14.3 |
| P |   | Right endometrial cyst | 42.9 |

Differences between an average value of free iron concentration in cystic fluid in the cancer group and an average value of free iron concentration in cystic fluid in the non-cancer group were assayed by nonparametric analysis (U-test of Mann-Whitney) in the same manner as in Example 1. Result is shown in FIG. 4.

Figure 4:
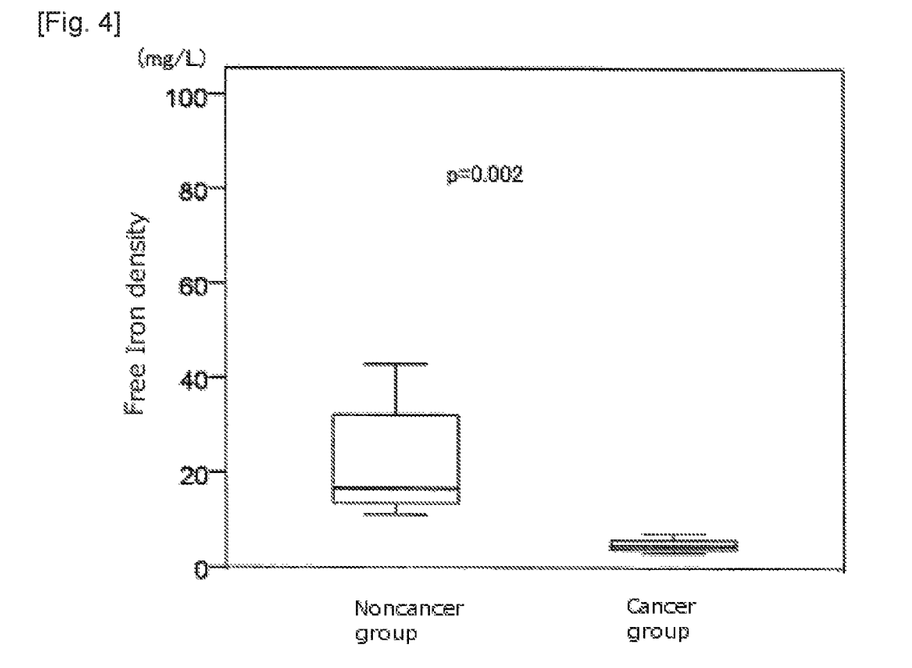
FIG. 4 is a graph showing the results of a difference in the average values of the concentration of free iron in the cystic fluid between, non-cancer group and cancer group, tested by non-parametric analysis (Mann-Whitney U-test).

Surprisingly, it became clear from the results shown in FIG. 4, the free iron concentration in the cyst fluid of endometriosis ovarian cysts is at most only 20% of the total iron concentration. Heretofore, it was believed that most of iron species contained in the cyst fluid are free iron. Now, the present inventors clarified such a fact that the main composition of chemical iron species contained in the cyst fluid heme iron and that free iron is only a small quantity.

Furthermore, it was confirmed that the likelihood that endometriosis ovarian cysts are cancerous can be determined by using the free iron concentration in cystic fluid as an indicator, because there is a significant difference between the mean value of the free iron concentration between two groups (cancer group=4.9 mg/L, cancer group=24.6 mg/L) (p=0.002).

The maximum value of the free iron concentration in the cyst fluid in cancer group was 7.1 mg/L (case N in Table 3), and the minimum value of the free iron concentration in the cyst fluid in non-cancer group was 11.0 mg/L (case F in Table 3). Therefore, the present inventors found that it is possible to determine that the endometriosis ovarian cysts may not be cancerous (may be benign ovarian cysts) when the free iron concentration in cystic fluid is 10 mg/L or more, while there is likelihood that the endometriosis ovarian cysts are cancerous if the free iron concentration in cystic fluid is higher than 0 mg/L and equal to or less than 10 mg/L.

Example 5

From the results of Example 2, the present inventors thought that likelihood of cancer can be determined by a presence ratio between oxy-heme and met-heme in the cyst.

To verify this supposition, the sensitivities of oxy-heme and met-heme were measured by a microplate reader (CORONA, SH-1200) for the cases shown in Table 4. Table 4 shows amounts of oxy-heme and met-heme in term of their sensitivities of at a marker wavelength of 580 nm for oxy-heme and at a marker wavelength of 620 nm for met-heme. The sensitivity ratio (=O.D 620 nm/O.D 580 nm) was calculated from the resulting sensitivities.

TABLE 4

| Case | | Clinical diagnosis | Sensitivity 580 nm oxy type marker | Sensitivity 620 nm met type marker | Sensitivity ratio = 620 nm/ 580 nm |
|---|---|---|---|---|---|
| A | 1 | Endometrioid adenocarcinoma | 0.26 | 0.11 | 0.42 |
|   | 2 | Right endometrial cyst | 0.56 | 0.44 | 0.78 |
| B | 1 | Left endometrial cyst ruptured | 0.29 | 0.21 | 0.74 |
|   | 2 | Right endometrial cyst non-ruptured | 0.41 | 0.28 | 0.70 |
| C |   | Left endometrial cyst | 0.38 | 0.29 | 0.76 |
| D |   | Left endometrial cyst | 0.98 | 0.53 | 0.54 |
| E |   | Left endometrial cyst | 0.40 | 0.27 | 0.68 |
| F | 1 | Right endometrial cyst | 0.25 | 0.17 | 0.69 |
|   | 2 | Left endometrial cyst | 0.43 | 0.23 | 0.54 |
| G | 1 | Left endometrial cyst | 0.18 | 0.12 | 0.68 |
|   | 2 | Right endometrial cyst | 0.79 | 0.53 | 0.67 |
| H |   | Left endometrial cyst | 0.57 | 0.44 | 0.76 |
| I |   | Right endometrial cyst | 0.57 | 0.39 | 0.68 |
| J |   | Left endometrial cyst | 0.27 | 0.22 | 0.80 |
| K |   | Right endometrial cyst | 0.44 | 0.35 | 0.80 |
| L | 2 | Left endometrial cyst | 0.55 | 0.37 | 0.67 |
| M |   | Left endometrial cyst | 0.23 | 0.14 | 0.62 |
| N |   | Right endometrial cyst | 0.35 | 0.29 | 0.83 |
| O | 1 | Serous adenocarcinoma | 0.09 | 0.03 | 0.27 |
|   | 2 | Serous adenocarcinoma | 0.73 | 0.10 | 0.14 |
| P |   | Clear cell adenocarcinoma | 0.13 | 0.05 | 0.45 |

Figure 5:
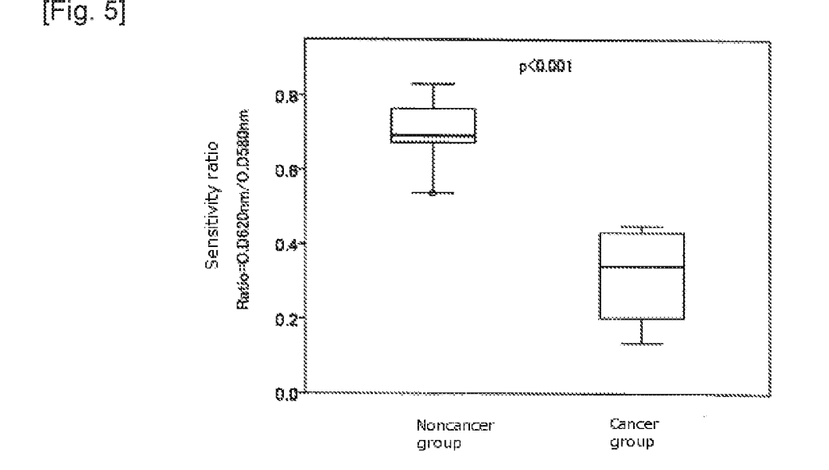
FIG. 5 is a graph showing the results of a difference in the average values of the sensitivity ratio (=O.D620 nm/O.D580 nm) in the cystic fluid between, non-cancer group and cancer group, tested by non-parametric analysis (Mann-Whitney U-test).

Difference between an average value of the sensitivity ratio of the cancer group and a mean value of the sensitivity ratio of the non-cancer group was assayed by the nonparametric analysis (U-test of Mann-Whitney). The results are shown in FIG. 5.

A significant difference in the mean value of the sensitivity ratio between the marker wavelength for oxy-heme and the marker wavelength for met-heme was observed between the groups (p<0.001). Therefore, it was confirmed that the likelihood that endometriosis ovarian cysts are cancerous can be determined by using the sensitivity ratio between oxy-heme and met-heme in cystic fluid as an index. In the most convenient practice, the sensitivity (or absorbance) at a wavelength in the vicinity of 620 nm which is a marker wavelength which is attributable to met-heme in cyst fluid, and a sensitivity (absorbance) at a wavelength of around 580 nm which is a marker wavelength which is attributable to oxy-heme are measured by a spectroscopic measuring instrument (spectrophotometer, densitometer, reflection spectroscopy device or the like) to obtain a sensitivity ratio (=O.D 620 nm/O.D 580 nm). Then it is possible to determine that there is a likelihood that the endometriosis ovarian cysts are not cancerous (benign ovarian cysts) when the sensitivity ratio is higher than 0.5, that the endometriosis ovarian cyst is cancerous when the sensitivity ratio is higher than 0 and lower than 0.5.

Example 6

The iron concentration in the cyst fluids was measured in further cyst fluid samples of endometriosis ovarian cysts as specimens in addition to the above Examples. The final total number of samples was 47 which includes 36 cases of non-cancer group and 11 cases of cancer group.

A number of specimens newly added is 27 (25 cases) in which 8 cases were cancerous cases (clear cell adenocarcinoma=5 cases, endometriosis adenocarcinoma=2 cases, mucosal adenocarcinoma=1 case). The newly added cases correspond to case Nos. 19-76 in Table 5 and Table 7. Case Nos. 1-17 contain specimens of Examples 1-5.

(1) The total iron concentration:
The total iron concentration in the cystic fluid was determined by ICP emission spectrometry in the same manner as in Example 1 for specimens of cyst fluid of endometriosis ovarian cysts.

(2) Heme iron concentration:
The heme iron concentration was quantified by Triton-MeOH assay coloring method in the same manner as in Example 3 for specimens of cyst fluid (3) Free iron concentration:
The free iron concentration was determined by chelating coloring method in the same manner as in Example 4 for specimens of cyst fluid.

(4) The presence ratio (sensitivity ratio) of oxy-heme and met-heme:
The presence ratio of oxy-heme and met-heme was determined in the same manner as in Example 5. An amount of oxy-heme and an amount of met-heme in the cystic fluid was measured in term of the sensitivities for a marker wavelength of 580 nm for oxy-heme and for a marker wavelength of 620 nm for met-heme respectively by using a microplate reader. The sensitivity ratio (=O.D 620 nm/O.D 580 nm) was calculated the resultant sensitivities.

Measured Results of the iron concentrations (1) to (3) are summarized in Table 5. Table 7 shows amounts of oxy-heme and of met-heme in cyst liquids and the presence ratio (sensitivity ratio) mentioned in above (4).

TABLE 5

| Case | | Clinical diagnosis | Total iron density (mg/L) | Heme-originated Fe (mg/L) | Free iron density (mg/L) |
|---|---|---|---|---|---|
| 1 | 1 | Endometrioid adenocarcinoma | 29.56 | 25.00 | 4.51 |
|   | 2 | Right endometrial cyst | 621.22 | 466.67 | 32.16 |
| 2 | 1 | Left endometrial cyst ruptured | 448.73 | 283.23 | 16.67 |
|   | 2 | Right endometrial cyst non-ruptured | 290.91 | 195.83 | 11.98 |
| 3 |   | Left endometrial cyst | 201.73 | 137.50 | 12.94 |
| 4 |   | Left endometrial cyst | 545.73 | 604.17 | 13.53 |
| 5 |   | Undifferentiated cancer | 11.85 | nd | nd |
| 6 |   | Left endometrial cyst | 67.15 | nd | nd |
| 7 | 1 | Right endometrial cyst | 315.20 | 123.77 | 19.05 |
|   | 2 | Left endometrial cyst | 204.96 | 237.15 | 16.67 |
| 8 | 1 | Left endometrial cyst | 65.28 | 93.38 | 14.29 |
|   | 2 | Right endometrial cyst | 300.26 | 402.42 | 16.67 |
| 9 |   | Left endometrial cyst | 322.50 | 374.26 | 33.33 |
| 10 | 1 | Right endometrial cyst | 230.13 | 304.60 | 23.81 |
| 11 |   | Left endometrial cyst | 78.42 | 92.64 | 11.90 |
| 12 |   | Right endometrial cyst | 1048.28 | 758.15 | 92.86 |
| 14 | 2 | Left endometrial cyst | 327.63 | 303.85 | 33.33 |
| 15 | 1 | Clear cell adenocarcinoma | 39.00 | 62.00 | 7.15 |
| 16 |   | Left endometrial cyst | 316.31 | 533.60 | 14.29 |
| 17 |   | Right endometrial cyst | 163.80 | 563.24 | 42.86 |
| 19 |   | Left endometrial cyst | 422.80 | 655.36 | 33.75 |
| 20 |   | Clear cell adenocarcinoma | 11.28 | 20.10 | 3.23 |
| 26 | 1 | Right endometrial cyst | 136.97 | 168.24 | 12.19 |
| 27 |   | Right endometrial cyst | 149.38 | 209.88 | 12.26 |
| 30 |   | Left endometrial cyst | 164.33 | 180.11 | 7.20 |
| 31 | 1 | Right endometrial cyst | 236.67 | 197.23 | 6.20 |
|   | 2 | Left endometrial cyst | 377.10 | 386.28 | 10.80 |
| 32 |   | Left endometrial cyst | 411.60 | 876.75 | 38.80 |
| 33 |   | Clear cell adenocarcinoma | 123.77 | 187.56 | 7.00 |
| 34 |   | Right endometrial cyst | 247.20 | 310.36 | 13.80 |
| 35 |   | Right endometrial cyst | 94.30 | 259.75 | 9.40 |
| 36 |   | Left endometrial cyst | 174.46 | 221.05 | 6.60 |
| 37 |   | Clear cell adenocarcinoma | 54.40 | 62.52 | 7.20 |
| 39 |   | Left endometrial cyst | 78.41 | 82.86 | 7.50 |
| 40 |   | Clear cell adenocarcinoma | 7.02 | 20.09 | 1.13 |

TABLE 5-continued

| Case | | Clinical diagnosis | Total iron density (mg/L) | Heme-originated Fe (mg/L) | Free iron density (mg/L) |
|---|---|---|---|---|---|
| 41 | | Clear cell adenocarcinoma | 64.40 | 30.13 | 5.00 |
| 42 | | Right endometrial cyst | 183.21 | 356.56 | 13.75 |
| 43 | | mucous adenocarcinoma | 14.18 | 3013 | 0.88 |
| 44 | 1 | Left endometrial cyst | 364.43 | 351.54 | 12.19 |
| | 2 | Left endometrial cyst | 530.66 | 401.76 | 13.44 |
| 62 | | Left endometrial cyst | 326.17 | 236.04 | 6.56 |
| 63 | | Left endometrial cyst | 735.53 | 1481.50 | 8.13 |
| 64 | 1 | Endometrioid adenocarcinoma | 4.04 | 10.04 | 1.53 |
| 65 | | Right endometrial cyst | 188.78 | 155.89 | 8.44 |
| 67 | 1 | Endometrioid adenocarcinoma | 2.96 | 7.53 | 0.84 |
| 68 | | Right endometrial cyst | 241.59 | 1396.13 | 18.44 |
| 76 | | Right endometrial cyst + adenofibroma | 129.10 | 190.84 | 11.25 |

Endometriosis ovarian cyst (chocolate cyst): n=36, endometriosis associated with ovarian cancer: n=11

TABLE 6

| | Endometriotic cysts Chocolate cyst (benign) | EAOC Endometriosis-associated ovarian cancer | P-value |
|---|---|---|---|
| Total iron (mg/L) | 244.4 ± 204.9 | 14.2 ± 36.6 | P < 0.001 |
| Heme-originated iron (mg/L) | 303.9 ± 324.4 | 27.8 ± 53.4 | P < 0.001 |
| Free iron (mg/L) | 13.5 ± 16.2 | 3.9 ± 2.7 | P < 0.001 |

Followings are observation resulting from Table 5 and Table 6.

(1) Total Iron Concentration (endometriosis: n=36, ovarian cancer: n=11)

It is confirmed from the results of measurement that the total iron concentration in cyst fluid of cases in which endometriosis ovarian cysts are cancerous (cancer group) is relatively lower than cases in which endometriosis ovarian cysts are not cancerous (non-cancer group, benign ovarian cyst) as same as the results of Example 1.

It is also confirmed that there is a significant difference between an average value of the total iron concentration in the cystic fluid of the cancer group (14.2 mg/L) and an average value of the total iron concentration in the cystic fluid of the non-cancer group (244.4 mg/L) (p=0.001). The difference was tested by non-parametric analysis (Mann-Whitney U-test). See Table 6.

From these results, it is confirmed that likelihood that endometriosis ovarian cysts are cancerous can be determined by using the total iron concentration in cystic fluid as an indicator, like the results of Example 1.

Statistically, when a cut-off value of the total iron concentration is set at 64.8 mg/L, the sensitivity is 90.9%, the specificity is 100%, the positive predictive value is 100% and the negative predictive value is 97.3%.

In this case, likelihood that endometriosis ovarian cysts is cancerous can be determined when the total iron concentration in cystic fluid is higher than 0 mg/L and lower than 64.8 mg/L.

There were 10 specimens whose total iron concentration is lower than the cut-off values: 64.8 mg/L and all of these specimens are cancerous specimens. There was no non-cancer specimen among them. On the contrary, there was only 1 case (case No. 33) that was cancer case and whose total iron concentration is higher than 64.8 mg/L among 47 specimens.

(2) Heme Iron Concentration (endometriosis: n=35, ovarian cancer: n=10)

Difference between an average value of the heme iron concentration of cyst fluid in the cancer group and an average value of the heme iron concentration in the cyst fluid in the non-cancer group was tested by non-parametric analysis (Mann-Whitney U-test). Result reveals that there is a significant difference between the average value of heme iron concentration in the cancer group (=27.6 mg/L) and the average value of the heme iron concentration in the non-cancer group (=303.9 mg/L) (p=0.001), in the same manner as in Example 3. See Table 6.

From these results, it was confirmed that it is possible to determine likelihood that endometriosis ovarian cysts are cancerous by using the heme iron concentration in cystic fluid as an indicator, like the results of Example 3, Statistically, when the cut-off value of the heme iron concentration is set as 72.7 mg/L, the sensitivity is 90%, the specificity is 100%, the positive predictive value is 100% and the negative predictive value is 97.2%.

In this case, likelihood that endometriosis ovarian cysts is cancerous can be determined when the heme iron concentration in cystic fluid is higher than 0 mg/L and equal to or lower than 72.7 mg/L.

There were 10 cases whose heme iron concentration is lower than the cut-off value: 72.7 mg/L and all of them were cancerous specimens. There was no non-cancer specimen among them. On the contrary, there was only 1 case (case No. 33) that was cancer case and whose total iron concentration is higher than 72.7 mg/L among 47 specimens as in the above (1).

(3) Free Iron Concentration (endometriosis; n=35, ovarian cancer; n=10)

In almost cases, the concentration of free iron in the cyst fluid of endometriosis ovarian cysts was equal to or less than 20% of the total iron concentration. This result is similar to the results of Example 4.

Heretofore, it was believed or estimated that most of iron species contained in the cyst fluid are free iron. However, results of Example 6 as well as Example 4 reveal such a fact that the main composition of the iron species contained in the cyst fluid is heme iron and a proportion of free iron is small.

It was confirmed also that there is a significant difference between an average value of the free iron concentration in cystic fluid in the cancer group (=3.9 mg/L) and an average value of the free iron concentration in cystic fluid in the non-cancer group (=13.5 mg/L) assayed by nonparametric analysis (Mann-Whitney U-test) (p<0.001). See Table 6. The result is same as in Example 4.

From these results, like the results of Example 4, it became clear that it is possible to determine likelihood that endometriosis ovarian cysts are cancerous by using the free iron concentration in cystic fluid as an indicator.

Statistically, when the cut-off value of the heme iron concentration is set as 7.18 mg/L, the sensitivity is 90.0%, the specificity is 91.4%, the positive predictive value is 75%, and the negative predictive value is 97.0%.

In this case, likelihood that endometriosis ovarian cysts is cancerous can be determined when the free iron concentration in cystic fluid is higher than 0 mg/L and equal to or lower than 7.18 mg/L.

There were 12 cases whose free iron concentration is lower than the cut-off value: 7.18 mg/L and 9 cases among them were cancerous specimens and 3 specimens (case Nos. 31, 36, 62) were non-cancer. On the contrary, there was only 1 case (case No. 33) that was cancer case and whose total iron concentration is higher than 7.18 mg/L among 47 samples.

Standardization of the Cut-Off Value

The cut-off values of (1) the total iron concentration, (2) heme iron concentration and (3) free iron concentration used in Examples 1, 3, 4, 6 may depend on equipment and reagents used in inspection and may vary in each laboratory or companies. The cut-off value vary also by calibration method used for measuring the concentration. In each laboratory, measurement of the iron concentration is performed for each subject on the base of a cut-off value for each iron concentration which is obtained in individual case and results are compared to use in judgment. Or, the judgment must be effected by using a standardized cut-off value which is optimized beforehand for the diagnostic device. Embodiments of the present invention show several methods of how to calculate the cut-off value.

Combination of Determination and Diagnosis

The determination and diagnosis can be done by either one of (1) the total iron concentration, (2) the heme iron concentration and (3) the free iron concentration, or any combination thereof.

It is possible to effect determination by a combination of results of (1) the total iron concentration or (2) the heme iron concentration with results of (3) the free iron concentration, because former two show substantially same values.

For example, high risk of cancer can't be determined even when the value of (1) or (2) is higher than the cut-off value. In this case, however, it is possible to determine high likelihood of cancer if a value of (3) is lower than a cutoff value. In Examples, 8 cases (case Nos, 30, 31, 33, 36, 39, 62, 63, 65) are such case and one case (case No. 33) was cancer case. If missing of cancer case for which surgical removal of cancer is necessary should be avoided, determination must be done with considering results of (1) or (2) and result of (3) free iron concentration.

It is also possible to combine at least one of the results of (1) to (3) with a result of (4) presence ration (sensitivity ratio) of oxy-heme and met-heme originated from heme iron which will be described later.

Determination of likelihood of canceration of endometriosis ovarian cysts can be performed advantageously by using a suitable combinations or by using the "iron concentration" as a biomarker.

(4) Presence Ratio (Sensitivity Ratio) of Oxy-Heme and Met-Heme

As described above, the heme include oxy-heme and met-heme. Amounts of the oxy-heme and met-heme in the cystic fluid in the cases shown in Table 5 were measured in the same manner as in Example 5. Namely, the sensitivity (or absorbance) at a wavelength around 620 nm which is a marker wavelength attributed to met-heme in cyst fluid and the sensitivity (absorbance) at a wavelength of around 580 nm which is a marker wavelength attributed to oxy-heme were measured by a microplate reader (CORONA, SH-1200) in a spectroscopic measurement instrument (absorption spectrophotometer, densitometer or reflection spectrum observation equipment) to obtain a sensitivity ratio (=O.D 620 nm/O.D 580 nm). The results are shown in Table 7.

TABLE 7

| Case | | Clinical diagnosis | 580 nm Oxy-form | 620 nm Met-form | Ratio = 620 nm/ 580 nm |
|---|---|---|---|---|---|
| 1 | 1 | Endometrioid adenocarcinoma | 0.182 | 0.029 | 0.159 |
|   | 2 | Right endometrial cyst | 0.321 | 0.199 | 0.620 |
| 2 | 1 | Left endometrial cyst ruptured | 0.201 | 0.128 | 0.637 |
|   | 2 | Right endometrial cyst non-ruptured | 0.258 | 0.136 | 0.527 |
| 3 |   | Left endometrial cyst | 0.226 | 0.133 | 0.588 |
| 4 |   | Left endometrial cyst | 0.717 | 0.265 | 0.370 |
| 5 |   | Undifferentiated cancer | nd | nd | nd |
| 6 |   | Left endometrial cyst | nd | nd | nd |
| 7 | 1 | Right endometrial cyst | 0.169 | 0.093 | 0.550 |
|   | 2 | Left endometrial cyst | 0.334 | 0.136 | 0.407 |
| 8 | 1 | Left endometrial cyst | 0.120 | 0.064 | 0.533 |
|   | 2 | Right endometrial cyst | 0.488 | 0.229 | 0.469 |
| 9 |   | Left endometrial cyst | 0.377 | 0.242 | 0.642 |
| 10 | 1 | Right endometrial cyst | 0.364 | 0.178 | 0.489 |
| 11 |   | Left endometrial cyst | 0.148 | 0.095 | 0.642 |
| 12 |   | Right endometrial cyst | 0.302 | 0.212 | 0.702 |
| 14 | 2 | Left endometrial cyst | 0.361 | 0.181 | 0.501 |
| 15 | 1 | Clear cell adenocarcinoma | nd | nd | nd |
| 16 |   | Left endometrial cyst | 0.178 | 0.089 | 0.500 |
| 17 |   | Right endometrial cyst | 0.220 | 0.161 | 0.732 |
| 19 |   | Left endometrial cyst | 0.028 | 0.023 | 0.821 |
| 20 |   | Clear cell adenocarcinoma | 0.105 | 0.034 | 0.324 |
| 26 | 1 | Right endometrial cyst | 0.031 | 0.020 | 0.645 |
| 27 |   | Right endometrial cyst | 0.029 | 0.028 | 0.897 |
| 30 |   | Left endometrial cyst | 0.007 | 0.010 | 1.429 |
| 31 | 1 | Right endometrial cyst | 0.019 | 0.020 | 1.053 |
|   | 2 | Left endometrial cyst | 0.022 | 0.015 | 0.682 |
| 32 |   | Left endometrial cyst | 0.027 | 0.018 | 0.593 |
| 33 |   | Clear cell adenocarcinoma | 0.243 | 0.155 | 0.638 |
| 34 |   | Right endometrial cyst | 0.025 | 0.016 | 0.640 |
| 35 |   | Right endometrial cyst | 0.021 | 0.015 | 0.714 |
| 36 |   | Left endometrial cyst | 0.019 | 0.018 | 0.947 |
| 37 |   | Clear cell adenocarcinoma | 0.116 | 0.075 | 0.647 |
| 39 |   | Left endometrial cyst | 0.105 | 0.070 | 0.667 |
| 40 |   | Clear cell adenocarcinoma | 0.031 | 0.004 | 0.129 |
| 41 |   | Clear cell adenocarcinoma | 0.005 | 0.004 | 0.800 |
| 42 |   | Right endometrial cyst | 0.066 | 0.033 | 0.500 |
| 43 |   | mucous adenocarcinoma | 0.111 | 0.030 | 0.270 |
| 44 | 1 | Left endometrial cyst | 0.032 | 0.019 | 0.594 |
|   | 2 | Left endometrial cyst | 0.053 | 0.034 | 0.642 |
| 62 |   | Left endometrial cyst | 0.026 | 0.017 | 0.654 |
| 63 |   | Left endometrial cyst | 0.061 | 0.045 | 0.738 |
| 64 | 1 | Endometrioid adenocarcinoma | nd | nd | nd |
| 65 |   | Right endometrial cyst | 0.109 | 0.06 | 0.587 |
| 67 | 1 | Endometrioid adenocarcinoma | 0.007 | 0.001 | 0.143 |
| 68 |   | Right endometrial cyst | 0.021 | 0.018 | 0.857 |
| 76 |   | Right endometrial cyst + adenofibroma | 0.019 | 0.014 | 0.737 | nd: not done

Difference between an average value of the sensitivity ratio of the cancer group and an average value of the sensitivity ratio of the non-cancer group was assayed by the nonparametric analysis (Mann-Whitney U-test) to find a significant difference between the sensitivity ratio of the marker wavelength for oxy-heme and the sensitivity ratio of the marker wavelength for met-heme (p=0.021). From this fact, it became clear that it is possible to determine likelihood that endometriosis ovarian cysts are cancerous by using the sensitivity ratio between oxy-heme and met-heme in cystic fluid as an index, as same as in Example 5.

When the cut-off value of the sensitivity ratio (=O.D 620 nm/O.D 580 nm=met/oxy) is set at 0.35, the sensitivity is 62.5%, the specificity is 100%, the positive predictive value is 100% and the negative predictive value is 92.1%.

In this case, we can determine that there is no likelihood that endometriosis ovarian cysts are cancerous when the cut-off value of the sensitivity ratio is not lower than 0.35 (benign ovarian cysts), and that there is likelihood that endometriosis ovarian cysts are cancerous when the sensitivity ratio is higher than 0 and lower than 0.35.

SUMMARY

From Examples 1-5, it became clear that it is possible to determine likelihood that endometriosis ovarian cysts are cancerous by measuring at least one chemical species of iron (total iron, heme iron or free iron) contained in the cyst fluid of endometriosis ovarian cysts and by using the iron concentration obtained as an indicator. In fact, it was confirmed that we can determine that there is a likelihood that endometriosis ovarian cysts are cancerous when the total iron concentration and the heme iron concentration in cystic fluid is higher than 0 mg/L and equal to or less than 63 mg/L, and that there is a likelihood that endometriosis ovarian cysts are cancerous when the free iron concentration in cystic fluid higher than 0 mg/L and equal to or less than 10 mg/L. On the contrary, if the total iron concentration and the heme iron concentration in cystic fluid is higher than 63 mg/L or if the free iron concentration in cyst fluid is higher than 10 mg/L, we can determined that endometriosis ovarian cysts is not cancerous (benign ovarian cyst).

It was also clarified that we can determine that endometriosis ovarian cysts are not cancerous (benign ovarian cysts) when the presence ratio of oxy-heme and met-heme: the sensitivity ratio of meth/oxy (=O.D 620 nm/O.D 580 nm) in the cyst is higher than 0.5, while, there is a likelihood that endometriosis ovarian cysts are cancerous when the sensitivity ratio is higher than 0 and lower than 0.5.

Thus, measured values of each iron concentration or the sensitivity ratio of met/oxy have technical importance as novel biomarkers for determining the likelihood of canceration of endometriosis ovarian cysts.

Results of Examples 1 to 5 are confirmed by Example 6 which was carried out for additional cases.

Among measurement method of the iron concentration in the cyst fluids of collected endometriosis ovarian cysts from a subject, the concentration of the "total iron" in the cyst fluid can be measured by ICP (inductively-coupled plasma) emission spectrometry or ICP mass spectrometry method for a collected the cyst fluid of endometriosis ovarian cyst as described above. Apparatus used in these methods, however, is very expensive and more than half a day is required before the measured result is obtained, so that these methods may not a generic or practical ones at the present days.

In contrast, the concentration of the "heme iron" or "free iron" can be measured by color developing method and reagents used in this method is inexpensive and results can be obtained after a lead time of several minutes, so that this technic can be a generic method to obtain results simply and more rapidly. Still more, a measured value of the concentration of the "total iron" is almost same as a measured value of the concentration of judgment for the heme iron". The result of judgment was also same both for the "total iron" and for the heme iron".

Such another embodiment such that part of a target tissue collected from an endometriosis ovarian cyst of a subject by "biopsy" can be also envisaged. In this case of biopsy, the risk of canceration or malignant transformation can be determined with greater accuracy in addition to pathological findings and/or pathological findings.

In the "biopsy" mentioned above or in "liquid biopsy" which was recently developed new technology to analyze components derived from a disease present in blood and body fluids, still another embodiment of the present invention can be also envisaged. In fact, a small quantity of cyst fluid of endometriosis ovarian cysts is sampled or collected by using an endoscope or the like to effect the measurement of the iron concentration and the risk characterization in real-time, so that it is possible to advance quickly to necessary treatment such as surgical treatment from the results obtained (for example, when there is high likelihood of cancer).

The following embodiments also can be envisaged:

(1) A method for determining likelihood that endometriosis ovarian cyst is cancerous by a testing and diagnostic device, including the steps of presenting a cut-off reference value calculated from a value of the iron concentration of a cyst fluid of endometriosis ovarian cyst which is anatomically benign and from a value of the iron concentration of the cyst fluid of endometriosis ovarian cyst which is cancerous, presented by an image presentation part of the testing and diagnostic device, obtaining a value of the iron concentration by measuring the iron concentration of cyst fluid of endometriosis ovarian cysts obtained from a subject in which malignant transformation is suspected, by a measuring unit for measuring the iron concentration of the device, comparing the measured value of the iron concentration and the iron concentration of the subject with the cut-off reference value to determine that there is a likelihood that the ovarian cyst of the subject is cancerous when the measured value of the iron concentration in the subject is lower than the cut-off reference value of the iron concentration, by a determining unit of the device, wherein the iron concentration is at least one of the total iron concentration, the heme iron concentration or the free iron concentration, the iron concentration is preferably a combination of the total iron concentration or heme iron concentration with the free iron concentration, and collecting a sample of the cyst fluid of endometriosis ovarian cyst from the subject by a sampling unit of the device.

(2) A testing and diagnostic device for determining a likelihood that endometriosis ovarian cyst is cancerous, including an iron concentration measurement unit for measuring the iron concentration in a cyst fluid of endometriosis ovarian cyst obtained from a subject in which malignant transformation is suspected, a data presentation part for presenting a cut-off value of the iron concentration which is calculated in advance from measured vales of the iron concentration in the cyst fluid of endometriosis ovarian cyst which is anatomically (pathologically) benign and from measured vales of the iron concentration in the cyst fluid of cancerous endometriosis ovarian cyst, a determining unit for judging that there is a likelihood that endometriosis ovarian cyst of the subject is cancerous when a measured vale of the iron concentration of the subject is compared with the cut-off value of the iron concentration and is significantly lower than the cut-off value, wherein, the iron concentration is at least one of (i) the total iron concentration, (ii) the heme iron concentration or (iii) the free iron concentration, the iron concentration is preferably a combination of the total iron concentration or the heme iron concentration with the free iron concentration, wherein, the cut-off value of each iron concentration is 63 mg/L for (i), 63 mg/L for (ii) and 10 mg/L for (iii) respectively, or the cut-off value of each iron concentration is 64.8 mg/L for (i), 72.7 mg/L for (ii) and 7.18 mg/L for (iii) respectively.

(3) A data acquisition method for determining a likelihood that endometriosis ovarian cysts are cancerous, characterized by including a step for measuring the iron concentration in the cyst fluid of endometriosis ovarian cysts of a subject, wherein, the determination is made in such a manner that there is likelihood that endometriosis ovarian cyst is cancerous when a measured value is below a reference cutoff value which was calculated in advance with respect to the iron concentration in cystic fluids, wherein, the iron concentration is at least one of (i) the total iron concentration, (ii) the heme iron concentration, or (iii) the free iron concentration.

wherein, the cut-off value of each iron concentration is 63 mg/L for (i), 63 mg/L for (ii) and 10 mg/L for (iii) respectively, or the cut-off value of each iron concentration is 64.8 mg/L for (i), 72.7 mg/L for (ii) and 7.18 mg/L for (iii) respectively.

(4) A data acquisition method for determining a likelihood of endometriosis ovarian cysts are cancerous, characterized by including an iron concentration measurement step for measuring the iron concentration in the cyst fluid of endometriosis ovarian cyst, wherein, the determination or judgment is made by at least one of following criteria (a) to (c):
(a) A likelihood of canceration of endometriosis ovarian cyst is determined when the total iron concentration in the cyst fluid is higher than 0 mg/L and equal to or less than 64.8 mg/L;
(b) A likelihood of canceration of endometriosis ovarian cyst is determined when the heme iron concentration in the cyst fluid is higher than 0 mg/L and equal to or less than 72.7 mg/L;
(c) A likelihood of canceration is determined when the free iron concentration in the cyst fluid is higher than 0 mg/L and equal to or less than 7.18 mg/L.

(5) A data acquisition method for determining a likelihood that endometriosis ovarian cysts are cancerous, characterized by including the steps of calculating a cut-off reference value of the iron concentration on the base of measured values of the iron concentration in a plurality of cyst fluids of anatomically benign endometriosis ovarian cysts, and measuring the iron concentration in a cyst fluid of endometriosis ovarian cysts from a subject in which malignant transformation is suspected, to obtain a measured value, wherein, the determination includes further the steps of comparing the measured value of the iron concentration in the subject with the cut-off reference value of iron concentration, and determining that there is likelihood that endometriosis ovarian cyst of the subject is cancerous when the measured value of the iron concentration in the subject is lower than the cut-off reference value of iron concentration, wherein, the iron concentration is either one of the total iron concentration, the heme iron concentration or the free iron concentration, wherein, the iron concentration is the heme iron concentration including met-heme and oxy-heme, including further a step for measuring a presence ratio of met-heme/oxy-heme in the cyst fluid of endometriosis ovarian cyst.

(6) A method for determining the treatment plan after determination of likelihood that endometriosis ovarian cyst is cancerous, characterized by including the steps of presenting a cut-off reference value of the iron concentration calculated from measured values of the iron concentration in the cyst fluids of anatomically benign endometriosis ovarian cysts and measured values of the iron concentration in the cyst fluids of cancerous endometriosis ovarian cysts, measuring the iron concentration in a cyst fluid of endometriosis ovarian cysts from a subject in which malignant transformation is suspected, to obtain a measured value, comparing the measured value of the iron concentration in the subject with the cut-off reference value of iron concentration, determining that there is likelihood that endometriosis ovarian cyst of the subject is cancerous when the measured value of the iron concentration in the subject is lower than the cut-off reference value of iron concentration, advancing to surgical treatment, when likelihood of malignant transformation is high, wherein the iron concentration is at least one of the total iron concentration, the heme iron concentration or the free iron concentration, the iron concentration is preferably the total iron concentration or a combination of heme iron concentration and the free iron concentration.

wherein, the iron concentration is the heme iron concentration including met-heme and oxy-heme, and including further a step of measurement of the presence ratio of met-heme/oxy-heme in the cyst fluid of the endometriosis ovarian cyst.

INDUSTRIAL APPLICABILITY

As described above, it is possible to acquire data for determining a likelihood that endometriosis ovarian cysts are cancerous by using the data acquisition method according to the present invention. Thus, it is possible to determine likelihood that endometriosis ovarian cysts are cancerous on the base of the data acquired by the data acquisition method according to the present invention. Further, it is possible to diagnose a likelihood that endometriosis ovarian cysts are cancerous by using the diagnostic device according to the present invention. Therefore, the method of data acquisition according to the present invention and the diagnosis apparatus according to the present invention contribute very highly in clinical practice.

Accordingly, the present invention is applicable for industry concerning diagnosis and medical for example.

DESCRIPTION OF THE CODE

1 Probe of an iron concentration measurement unit
2, 2' Insertion member
3 Probe for image forming part
10, 20, 30 Diagnostic device

The invention claimed is:
1. A method by a diagnostic device, the method comprising:
   obtaining a cystic fluid sample from a subject;
   detecting wavelength sensitivities of a met-heme attribute and an oxy-heme attribute respectively by measuring the cystic fluid sample by a spectrometer.
2. A diagnostic device comprising:
   a spectrometer configured to obtain a cystic fluid sample from a subject and to measure wavelength sensitivities of a met-heme attribute and an oxy-heme attribute respectively by measuring the cystic fluid sample.
3. The diagnostic device according to claim 2, further comprising:
   a probe configured to be inserted into a vagina of a research subject.

4. The diagnostic device according to claim 3, wherein said probe comprises an image forming unit configured to visualize an endometriosis ovarian cyst.

5. The diagnostic device according to claim 4, wherein said probe comprising said image forming unit is configured to be inserted into the vagina of the research subject.

6. The diagnostic device according to claim 4, wherein said image forming unit is an ultrasound image forming unit.

7. The method according to claim 1, further comprising:
inserting a probe, comprising the spectrometer, into a vagina of the subject;
performing, by the spectrometer, spectroscopy by emitting light onto the cystic fluid sample while the probe is inserted into the vagina of the subject; and
measuring the wavelength sensitivities of the met-heme attribute and the oxy-heme attribute from the cystic fluid sample by the spectroscopy,
wherein the light comprises at least one of an infrared wavelength and a near-infrared wavelength.

8. The method according to claim 7,
wherein the spectroscopy comprises transmissive spectroscopy.

9. The method according to claim 7,
wherein the spectroscopy comprises reflective spectroscopy.

10. The method according to claim 7, further comprising:
detecting whether the wavelength sensitivities of the met-heme attribute and the oxy-heme attribute are within at least one of a plurality of predetermined ratios.

11. The method according to claim 10,
wherein a first one of the predetermined ratios corresponds to the wavelength sensitivities of the met-heme attribute and the oxy-heme attribute being not lower than 0.80,
wherein a second one of the predetermined ratios corresponds to the wavelength sensitivities of the met-heme attribute and the oxy-heme attribute being lower than 0.80 and not lower than 0.35, and
wherein a second one of the predetermined ratios corresponds to the wavelength sensitivities of the met-heme attribute and the oxy-heme attribute being lower than 0.35.

12. The method of claim 1,
wherein the wavelength sensitivities of the met-heme attribute and the oxy-heme attribute comprise optical densities (O.D.),
wherein detecting the wavelength sensitivities of the met-heme attribute and the oxy-heme attribute comprises setting a first marker wavelength to 620 nm±20 nm and a second marker wavelength to 580 nm±20 nm,
wherein the first marker wavelength corresponds to the met-heme attribute, and
wherein the second marker wavelength corresponds to the oxy-heme attribute.

* * * * *